United States Patent [19]

Bosies et al.

[11] Patent Number: 4,517,183

[45] Date of Patent: May 14, 1985

[54] N-SUBSTITUTED AZIRIDINE-2-CARBOXYLIC ACID DERIVATIVES

[75] Inventors: Elmar Bosies, Weinheim; Wolfgang Kampe, Heddesheim; Max Thiel, Mannheim; Uwe Bicker, Lorsch; Dietmar Boerner, Lampertheim-Hüttenfeld, all of Fed. Rep. of Germany

[73] Assignee: Boehringer Mannheim GmbH, Mannheim, Fed. Rep. of Germany

[21] Appl. No.: 495,548

[22] Filed: May 17, 1983

Related U.S. Application Data

[60] Division of Ser. No. 236,375, Feb. 20, 1981, Pat. No. 4,397,848, which is a continuation of Ser. No. 117,165, Jan. 3, 1980, abandoned.

[30] Foreign Application Priority Data

Feb. 21, 1979 [DE] Fed. Rep. of Germany ....... 2906603

[51] Int. Cl.$^3$ ................. C07D 203/22; C07D 401/12; C07D 403/12; A61K 31/395
[52] U.S. Cl. .................................... 514/183; 548/263; 548/264; 260/239 E; 548/265; 548/266; 260/330.3; 548/267; 548/268; 260/330.9; 548/269; 548/323; 544/153; 548/324; 548/374; 544/155; 548/336; 514/241; 544/156; 514/252; 514/256; 544/157; 514/266; 514/314; 544/174; 514/340; 514/359; 544/175; 514/365; 514/406; 544/176; 514/444; 514/459; 544/182; 544/234; 544/235; 544/238; 544/251; 544/255; 546/48; 546/65; 546/90; 546/115; 546/116; 546/183; 548/153; 548/183; 548/184; 548/185; 548/187; 548/189; 548/209; 548/210; 548/213; 548/214; 514/461; 514/469
[58] Field of Search .............. 260/239 E, 330.3, 330.9; 424/244, 273 P, 273 R, 269, 263, 275, 256, 258, 250, 251, 253, 278; 544/234, 235, 238, 255, 251, 276, 277, 153, 155, 156, 157, 174, 175, 176; 546/48, 65, 90, 115, 116, 183; 548/153, 183, 184, 187, 185, 189, 209, 210, 213, 214, 263, 264, 265, 266, 267, 268, 269, 323, 324, 374, 336

[56] References Cited

FOREIGN PATENT DOCUMENTS 2731264 2/1979 Fed. Rep. of Germany .

OTHER PUBLICATIONS

Bosies, Chem. Abs. 94, 15542t, (1980).
Kostyanovskii 85, 192460, (1976).
Kostyanovskii 81, 25474, (1974).
Kostyanovskii 87, 101491, (1977).

Primary Examiner—Mark L. Berch
Attorney, Agent, or Firm—Sprung, Horn, Kramer & Woods

[57] ABSTRACT

The present invention provides pharmaceutical compositions containing N-substituted aziridine-2-carboxylic acid derivatives of the general formula:

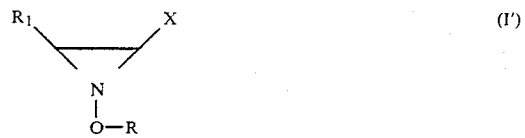

wherein X is a carboxyl, a cyano, an alkoxycarbonyl or an optionally substituted carbamoyl radical, R is a hydrogen atom, an aliphatic hydrocarbon radical which is saturated or can contain one or more unsaturations and can be substituted one or more times by halogen, alkoxy, hydroxyl, dialkylamino, dialkylaminoxy, cycloalkylamino, acylamino, acyl, nitro, alkylthio, alkylsulphinyl, alkylsulphonyl, cyano, carboxyl, alkoxycarbonyl or carbamoyl or by cycloalkyl or cycloalkenyl radicals optionally carrying alkyl, alkoxy or alkoxycarbonyl radicals, optionally interrupted by hetero atoms and optionally bridged, or by an aryl, hetaryl, aryloxy, arylthio, acyloxy, alkoxycarbonylamino or isothioureido radical, or R is a cycloalkyl or cycloalkenyl radical optionally substituted by alkyl, alkoxy or oxo groups, optionally interrupted by hetero atoms and optionally bridged, or is an aryl or hetaryl radical which can be substituted one or more times by halogen, alkoxy, alkyl, hydroxyl, alkoxycarbonyl, carbamoyl, dialkylamino, cycloalkylamino, acylamino, nitro, cyano, acyl, alkylthio, alkylsulphinyl, alkylsulphonyl, sulphamoyl, phenyl, trifluoromethyl, aryloxy, acyloxy or methylenedioxy radicals and $R_1$ is a hydrogen atom or an alkyl or phenyl radical; and the pharmacologically acceptable salts thereof, in admixture with a pharmaceutical diluent or carrier. The present invention also provides, as new compounds, N-substituted aziridine-2-carboxylic acid derivatives of general formula (I') but with the proviso that when X is a carbamoyl or alkoxycarbonyl radical and $R_1$ is a hydrogen atom, R is not a methyl, ethyl, isopropyl or benzyl radical; and the pharmacologically acceptable salts thereof, and also provides processes for the preparation of these new compounds. Furthermore, the present invention is concerned with the use of the compounds of general formula (I') and of the pharmacologically acceptable salts thereof for combating diseases associated with a weakening of the immune system.

13 Claims, No Drawings

N-SUBSTITUTED AZIRIDINE-2-CARBOXYLIC ACID DERIVATIVES

This is a division of application Ser. No. 236,375, filed Feb. 20, 1981, now U.S. Pat. No. 4,397,848, which is a continuation of Ser. No. 117,165, filed Jan. 31, 1980, now abandoned.

The present invention is concerned with N-substituted aziridine-2-carboxylic acid derivatives, processes for the preparation thereof and pharmaceutical compositions containing them.

The new N-substituted aziridine-2-carboxylic acid derivatives according to the present invention are compounds of the general formula:

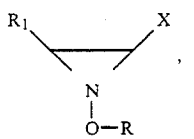

wherein X is a carboxyl, or cyano, an alkoxycarbonyl or an optionally substituted carbamoyl radical, R is a hydrogen atom, an aliphatic hydrocarbon radical which can be saturated or can contain one or more unsaturations and which can be substituted one or more times by halogen, alkoxy, hydroxyl, dialkylamino, dialkylaminoxy, cycloalkylamino, acylamino, acyl, nitro, alkylthio, alkylsulphinyl, alkoxysulphonyl, cyano, carboxyl, alkoxycarbonyl or carbamoyl or by cycloalkyl or cycloalkenyl radicals optionally carrying alkyl, alkoxy or alkoxycarbonyl radicals, optionally interrupted by hetero atoms and optionally bridged, or by an aryl, hetaryl, aryloxy, arylthio, acyloxy, alkoxycarbonylamino or isothioureido radical, or R is a cycloalkyl or cycloalkenyl radical optionally substituted by alkyl, alkoxy or oxo groups, optionally interrupted by hetero atoms and optionally bridged, or is an aryl or hetaryl radical which can be substituted one or more times by halogen, alkoxy, alkyl, hydroxyl, alkoxycarbonyl, carbamoyl, dialkylamino, cycloalkylamino, acylamino, nitro, cyano, acyl, alkylthio, alkylsulphinyl, alkylsulphonyl, sulphamoyl, phenyl, trifluoromethyl, aryloxy, acyloxy or methylenedioxy radicals and $R_1$ is a hydrogen atom or an alkyl or phenyl radical, with the proviso that when X is a carbamoyl or an alkoxycarbonyl radical and $R_1$ is a hydrogen atom, R is not a methyl, ethyl, isopropyl or benzyl radical; and the pharmacologically compatible salts thereof.

The compounds of general formula (I) possess asymmetrical carbon atoms and can occur as cis-trans isomers. Consequently, the present invention also includes within its scope all stereoisomeric forms, as well as mixtures thereof. A separation of the stereoisomeric forms which it may be desired to carry out, can be done so in known manner.

Published Federal Republic of Germany Patent Specifications Nos. 27 27 550, 26 56 323 and 27 31 264 describe immune-stimulating aziridine-2-carboxylic acid derivatives which are acylated on the cyclic nitrogen atom.

Surprisingly, we have now found a group of aziridine-2-carboxylic acid derivatives which carry on the cyclic nitrogen atom, instead of an acyl radical, an alkoxy, aryloxy or hetaryloxy substituent, display a distinctly better immune stimulation and, in addition, no noteworthy side effects. Therefore, these compounds are outstandingly suitable for combating diseases which involve a weakening of the immune system.

Furthermore, we have found in animal experiments that the new compounds according to the present invention possess an effectiveness against malign tumors and, therefore, can be used as adjuvants for an immune therapy of malign tumors. We have also found that these new compounds are able to reduce or partly to compensate the bone marrow toxicity of X-rays and of cytostatic drugs.

Some of the compounds of general formula (I), in which $R_1$ is hydrogen and X is an alkoxycarbonyl or a carbamoyl radical, are known from the literature (see, for example, Chem. Abs., 81, 25474t and 85, 192460z). However, these literature references do not contain any mention of a pharmacological effectiveness of these compounds.

The present invention is also concerned with processes for the preparation of compounds of the general formula (I), as well as with the use of aziridine-2-carboxylic acid derivatives substituted on the cyclic nitrogen atom of the general formula:

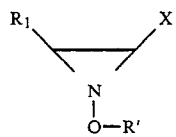

wherein X is a carboxyl, a nitrile, an alkoxycarbonyl or an optionally substituted carbamoyl radical, R' is a hydrogen atom, an aliphatic hydrocarbon radical which can be saturated or can contain one or more unsaturations and which can be substituted one or more times by halogen, alkoxy, hydroxyl, dialkylamino, dialkylaminoxy, cycloalkylamino, acylamino, acyl, nitro, alkylthio, alkylsulphinyl, alkylsulphonyl, nitrilo, carboxyl, alkoxycarbonyl or carbamoyl or by cycloalkyl or cycloalkenyl radicals optionally carrying alkyl, alkoxy or alkoxycarbonyl radicals, optionally interrupted by hetero atoms and optionally bridge, or by an aryl, hetaryl, aryloxy, arylthio, acyloxy, alkoxycarbonylamino or isothioureido radical, or R is a cycloalkyl or cycloalkenyl radical optionally substituted by alkyl, alkoxy or oxo groups, optionally interrupted by hetero atoms and optionally bridged, or is an aryl or hetaryl radical which can be substituted one or more times by halogen, alkoxy, alkyl, hydroxyl, alkoxycarbonyl, carbamoyl, dialkylamino, cycloalkylamino, acylamino, nitro, cyano, acyl, alkylthio, alkylsulphinyl, alkylsulphonyl, sulphamoyl, phenyl, trifluoromethyl, aryloxy, acyloxy or methylenedioxy radicals and $R_1$ is a hydrogen atom or an alkyl or phenyl radical, as well as of their pharmacologically acceptable salts for combating disease involving a weakening of the immune system.

The immune-stimulating action of the compounds according to the present invention can be demonstrated by:

1. the increase of the leucocytes after oral or intravenous administration of the above-mentioned compounds,
2. the increase of the lymphocyte transformation, measured with the help of the incorporation of radioactively-marked thymidine into human lymphocytes after incubation with the above-mentioned compounds (cf. in this regard K. Resch in "Praxis der Immunologie", editor K. O. Vorlander, Thieme-Verlag, Stuttgart, 1976), and 3. with the help of animal experimental infections in mice.

In the case of the last-mentioned investigation, we have, surprisingly, found that the additional administration of the compounds of general formula (I') to a known bacteriostatically-acting chemotherapeutic agent, for example chloramphenicol, shows a more distinct therapeutic effect than the sole administration of the bacteriostatic chemotherapeutic agent.

Therefore, the present invention also provides pharmaceutical compositions which, in addition to a compound of general formula (I') and appropriate carriers and adjuvants, contains a chemotherapeutic agent. Chemotherapeutic agents are to be understood to be commercially available compounds with an antimicrobial action, for example, penicillins, cephalosporins, sulphonamides, aminoglycoside antibiotics, tetracyclines and the like. The synergistic effect is clearly shown, for example, in the above-described pharmaceutical combinations which contain an immune stimulant from the group of compounds of general formula (I) and the bacteriostatically-acting chemotherapeutic compound chloramphenicol.

In the definition of the substituents X, R, R' and $R_1$ as such or in combination with other groupings, for example, in alkoxy, alkoxycarbonyl, dialkylamino, dialkylaminoxy, alkylthio, alkylsulphinyl and alkylsulphonyl radicals, the alkyl radicals are to be understood to be straight-chained or branched hydrocarbon chains containing up to 8 and preferably up to 6 carbon atoms, the preferred radicals thereby including the methyl, ethyl, n-propyl, isopropyl, n-butyl, sec.-butyl, tert.-butyl, n-pentyl and n-hexyl radicals. The preferred dialkylamino radical is the dimethylamino radical, the preferred dialkylaminoxy radical is the 2-cyanoaziridin-1-yloxy radical and the preferred acylamino radicals are the formamido, acetamido and benzamido radicals.

An aliphatic hydrocarbon radical R or R' containing one or more unsaturations is to be understood to be a radical containing 3 to 8 and preferably 3 to 5 carbon atoms, the double and/or triple bonds being at any desired point of the chain. Especially preferred radicals of this type include the vinyl, allyl, methallyl, crotyl, 1-methylprop-2-enyl, propargyl, but-2-ynyl, 1-methylbut-2-ynyl and pent-3-ynyl radicals.

The cycloalkyl or cycloalkenyl radicals in the definition of the substituents R and R' are to be understood to be those containing 3 to 10 carbon atoms, especially the cyclopropyl, cyclopentyl, cyclohexyl, cyclohexenyl and cycloheptenyl radicals, as well as cycloalkyl radicals bridged with up to 3 carbon atoms, for example, the norbornyl and adamantyl radicals. The cycloalkyl and cycloalkenyl radicals interrupted by hetero atoms are preferably tetrahydrofuryl, tetrahydropyranyl and thianyl radicals, as well as optionally substituted piperidinyl, morpholinyl and pyrrolidinyl radicals, and also the methylpiperazinyl radical.

The aryl radicals in the definition of the substituents R and R' are as such or in aryloxy or arylthio groupings, aromatic carbocyclic radicals, the phenyl, naphthyl, anthracenyl, phenanthrenyl and fluorenyl radicals being preferred.

The hetaryl radical as substituent R and R' is a 5- or 6-membered aromatic ring system with one or more hetero atoms selected from oxygen, sulphur and nitrogen, which latter can be alkylated or acylated. The hetaryl radical can also be condensed with one or two benzene rings or with a further aromatic heterocyclic system. Preferred radicals of this type include the pyridyl, quinolyl, furyl, thienyl, benzofuryl, imidazolyl, pyrazolyl, thiazolyl, pyrimidinyl, pyridazinyl, s-triazolyl, 3-triazinyl and purinyl radicals.

According to the present invention, halogen is preferably fluorine, chlorine, or bromine.

The acyl radicals in the definition of the substituents R and R' are, as such or in acylamino and acyloxy groupings, acid residues of organic carboxylic acids and of sulphonic acids, preferred radicals of this type including the formyl, acetyl, benzoyl, furoyl, tosyl and methylsulphonyl radicals.

The carbamoyl radical of the substituent X is optionally substituted by lower alkyl, cycloalkyl, aryl and/or acyl radicals.

The new compounds of general formula (I) according to the present invention can be prepared in known manner, for example by one of the following methods:

(a) a compound of the general formula:

in which $R_1$ and X have the same meanings as above, $Hal_1$ and $Hal_2$ are chlorine or bromine atoms and L is a hydrogen atom or in which $Hal_1$ and L together represent a valency bond, is reacted with a hydroxylamine derivative of the general formula:

$$R—O—NH_2 \qquad (III),$$

in which R has the same meaning as above; or (b) a compound of the general formula:

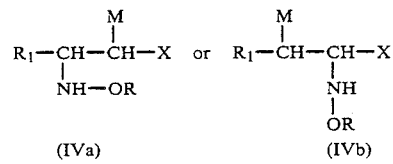

or a salt thereof, in which $R_1$, R and X have the same meanings as above and M is a chlorine or bromine atom or the group —A—Z, A being an oxygen or sulphur atom and Z being a hydrogen atom or a grouping which, together with oxygen or sulphur, can easily be eliminated, is treated with a reagent splitting off M—H; or (c) a compound of the general formula:

in which R and $R_1$ have the same meanings as above and X' is a —CH=$NOR_2$ radical, $R_2$ being a hydrogen atom or an alkyl radical, is treated with a reagent splitting off water or an alcohol; or (d) an oxazolidinone of the general formula:

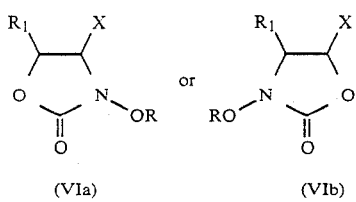

(VIa)     (VIb)

in which R, $R_1$ and X have the same meanings as above, is subjected to thermolysis; or (e) a compound of the general formula:

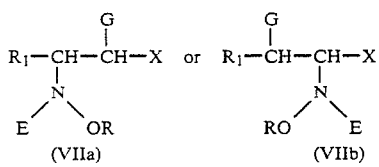

(VIIa)     (VIIb)

in which R, $R_1$ and X have the same meanings as above and G is a hydrogen, chlorine or bromine atom and E is a chlorine or bromine atom, a trialkylamino radical or an arylsulphonic acid residue, is treated with a reagent splitting off E—G; or (f) an epoxide of the general formula:

(VIII)

in which $R_1$ and X have the same meanings as above, is reacted with a hydroxylamine derivative of general formula (III); whereafter, if desired, in a compound obtained of general formula (I), a substituent X or R is converted into a different substituent X or R as defined above and, if desired, a compound obtained of general formula (I) is converted into a pharmacologically acceptable salt.

In the case of processes (a) and (b), as reagent splitting off hydrogen halide there is used a base, especially a tertiary amine, for example triethylamine, triethanolamine, diazabicycloalkenes or the like. Alcohols are hereby used, for example methanol, ethanol or butanol, but also inert solvents, such as methylene chloride, dioxane, benzene or toluene. Solvents such as dimethylformamide or dimethyl sulphoxide can also be used very satisfactorily. Furthermore, in some cases, it is especially preferred to use an alcoholate, for example sodium methylate or sodium ethylate, in the corresponding alcohol. In the case of process (b), especially when the group —A—Z is a hydroxyl group, as agent splitting off water, it is especially preferred to use triphenylphosphine in the presence of carbon tetrachloride and triethylamine, whereby, as a rule, methylene chloride or chloroform is used as solvent. However, the splitting off of water can also be carried out with sulphuric acid.

In the case of process (c), use can be made of the usual methods known from the literature for the conversion of an oxime group into a nitrile group, for example, the splitting off of water or alcohol with the help of thionyl chloride, phosphorus pentachloride, phosphorus pentoxide, trifluoroacetic anhydride, dicyclohexylcarbodiimide and the like. As adjuvant base, there can hereby be used amines, for example triethylamine, pyridine and the like. The reaction with triphenylphosphine in the presence of carbon tetrachloride and triethylamine takes place under very mild conditions. As solvent, it is hereby preferred to use methylene chloride or chloroform.

Oxazolidinones of general formula (VIa) or (VIb) are, in the case of process (d), as a rule thermolyzed, without the use of a solvent, in the presence of a base, for example triethanolamine or dicyclohexylethylamine, the reaction product distilling off during the course of the thermolysis. The temperature used for the thermolysis is generally from 170° to 250° C.

In the case of process (e), reagents splitting off E—G, when G is a hydrogen atom, are preferably alcoholates, such as alkali metal methylates or alkali metal ethylates, in the corresponding alcohols. However, use can also be made of tertiary amines, for example, triethylamine, triethanolamine, dicyclohexylethylamine or diazabicycloundecene, in solvents, for example, methanol, ethanol, benzene, toluene, diethyl ether or dioxane. When E and G are chlorine or bromine atoms, for the splitting off use can be made of conventional dehalogenation agents, preferably of zinc or sodium.

In the case of process (f), an epoxide of general formula (VIII) can be reacted with a hydroxylamine derivative of general formula (III) and the aminoalcohol thus obtained is then dehydrated, as described in the case of process (b), to give an aziridine derivative of general formula (I). However, for the conversion of the epoxide into an aziridine, use can also be made of compounds such as R—O—N—P(O)(OAlk)$_2^-$ or Ph$_3$P=N—OR, in which R has the same meaning as above, Ph is a phenyl radical and Alk is a lower alkyl radical, for example a methyl or ethyl radical.

Examples of subsequent conversions of a substituent R or X in compounds of general formula (I) into a different substituent R or X include the following: the reaction of compounds in which X is an alkoxycarbonyl radical to give compounds in which X is a carbamoyl radical;

the conversion of compounds in which X is a carbamoyl radical into compounds in which X is a nitrile group; the saponification of a nitrile group X in compounds of general formula (I) to give a carbamoyl or carboxyl group X;

the esterification of a carboxyl radical X to give an alkoxycarbonyl radical X or, in reversal of this reaction, the saponification of compounds in which X is an alkoxycarbonyl or carbamoyl radical to give compounds in which X is a carboxyl group, as well as the etherification of compounds in which R is a hydroxyl group to give compounds of general formula (I) in which the substituent R has the other meanings given above.

The conversion of an ester grouping into an amide grouping can be carried out with gaseous ammonia in an organic solvent, preferably in methanol or ethanol, or aqueous ammonia solution at 0° to 25° C. The desired amide either precipitates out of the reaction mixture or can be isolated therefrom, for example by column chromatography.

For the conversion of a carbamoyl group into a nitrile group, use can be made of dehydration methods known from the literature, use preferably being made of a mixture of triphenylphosphine, carbon tetrachloride and triethylamine. As solvent, there is usually employed a halogenated hydrocarbon, for example methylene chloride or chloroform, but acetonitrile can also be used. As a rule, the desired nitrile is isolated from the reaction mixture by distillation.

Saponification of a nitrile group to give a carbamoyl or carboxyl group, esterification of a carboxyl group to give an alkoxycarbonyl radical, as well as saponification of an alkoxycarbonyl or carbamoyl radical to give a carboxyl group, are, as a rule, carried out by the methods known from the literature.

The etherification of 1-hydroxyaziridine-2-carboxylic acid derivatives to give the corresponding alkoxy, aryloxy or hetaryloxy derivatives also takes place by the methods known from the literature, preferably by the reaction with compounds of the general formula R″Y, in which R″ has the same meaning given above for R, apart from hydrogen, and Y is a reactive acid residue, preferably a halogen atom or a mesyloxy or tosyloxy radical. This reaction is preferably carried out in an alcohol, for example methanol or ethanol, in the presence of the corresponding alkali metal alcoholate. However, it is also possible to work in a solvent such as dimethyl sulphoxide or dimethylformamide, in the presence of a hydride, for example sodium hydride.

Some starting materials required for the preparation of the compounds according to the present invention are known compounds. Others can be prepared analogously to the methods described for the preparation of the known compounds.

Compounds of general formula (IVa) can be obtained, for example, by the addition of O-substituted hydroxylamine derivatives on to activated, preferably bromine-activated acrylic acid derivatives according to conventional methods. The oximes of general formula (V) can be obtained in known manner from the corresponding aldehydes and the hydroxylamine derivatives. For the preparation of compounds of general formula (VI), N-OR-substituted serine or isoserine derivatives are preferably cyclized with phosgene, chloroformic acid esters and the like.

For the preparation of pharmaceutical compositions with immune-stimulating action, the compounds of general formula (I') are mixed in known manner with appropriate pharmaceutical carrier substances and formed, for example, into tablets or dragees or, with the addition of appropriate adjuvants, suspended or dissolved in water or in an oil, for example olive oil, and placed into hard gelatine capsules. Since the active material is acid labile, the composition is either provided with a coating which only dissolves in the alkaline intestine medium or is admixed with an appropriate carrier material, for example, a high molecular weight fatty acid or carboxymethylcellulose. Examples of solid carrier materials include starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents.

As injection medium, it is preferred to use water which contains the additives usual in the case of injection solutions, such as stabilizing agents, solubilizing agents or weakly alkaline buffers. Examples of additives of this type include dimethyl sulphoxide, dimethylformamide, N-methylpyrrolidone, phosphate and citrate buffers, ethanol, complex formers (such as ethylenediamine-tetraacetic acid and the non-toxic salts thereof) and high molecular weight polymers (such as liquid polyethylene oxide) for viscosity regulation.

For combating diseases which involve a weakening of the immune system, the pharmacologically active compounds of general formula (I') can be administered in individual doses of 1 to 600 and preferably of 50 to 500 mg., these individual doses being administered one or more times a day, according to need.

For pharmaceutical combinations in which the compounds of general formula (I') are present together with a chemotherapeutic agent, in general, there are used the same galenical forms of composition as described above for the individual compounds. The two active materials, i.e. the immune stimulant and the chemotherapeutic agent, are usually present in the composition in a weight ratio of 10:1 to 1:10, an equimolar ratio of the two components having proved to be advantageous.

A suitable composition comprises, for example, 100 mg. chloramphenicol as chemotherapeutic agent and 33.3 mg. 2-cyano-1-ethoxyaziridine, as well as appropriate carrier materials, such as starch, and is produced in the form of 250 mg. tablets which, as a rule, are taken orally twice a day.

Apart from the compounds described in the following Examples, the following compounds are also preferred according to the present invention:
2-cyano-1-hydroxyaziridine
2-cyano-1-n-propoxyaziridine
1-sec.-butoxy-2-cyanoaziridine
1-tert.-butoxy-2-cyanoaziridine
2-cyano-1-pentyloxyaziridine
2-cyano-1-hexyloxyaziridine
1-(3-chloropropoxy)-2-cyanoaziridine
2-cyano-1-(2,2,2-trichloroethoxy)-aziridine
2-cyano-1-(2-fluoroethoxy)-aziridine
2-cyano-1-(2-hydroxyethoxy)-aziridine
2-cyano-1-(2,3-dihydroxypropoxy)-aziridine
2-cyano-1-(2-methoxyethoxy)-aziridine
2-cyano-1-tetrahydrofurfuryloxyaziridine
2-cyano-1-(tetrahydropyran-2-yloxy)-aziridine
2-cyano-1-(2-phenoxyethoxy)-aziridine
1-(2-acetoxyethoxy)-2-cyanoaziridine
2-cyano-1-(3-N,N-dimethylaminopropoxy)-aziridine
1,2-bis-(2-cyano-1-aziridinyloxy)-ethane
2-cyano-1-(2-morpholinoethoxy)-aziridine
1-(2-acetamidoethoxy)-2-cyanoaziridine
1-(2-benzamidoethoxy)-2-cyanoaziridine
1-(1-acetylpiperidin-4-ylmethoxy)-2-cyanoaziridine
2-cyano-1-(2-oxazolidinon-5-ylmethoxy)-aziridine
2-cyano-1-(2-nitroethoxy)-aziridine
2-cyano-1-(3-methylthiopropoxy)-aziridine
2-cyano-1-(2-methylsulphinylethoxy)-aziridine
2-cyano-1-(2-methylsulphonylethoxy)-aziridine
S-[2-(2-cyanoaziridin-1-yloxy)-ethyl]-isothiourea
2-cyano-1-(thian-3-yloxy)-aziridine
2-cyano-1-(2-phenylthioethoxy)-aziridine
2-cyano-1-(2-cyanoethoxy)-aziridine
2-cyanoaziridin-1-yloxy acetic acid
ethyl 2-cyanoaziridin-1-yloxy acetate
2-cyanoaziridin-1-yloxy acetamide
methyl 2-(2-cyanoaziridin-1-yloxy)-propionate
2-cyano-1-methallyloxyaziridine
2-cyano-1-(1-methylprop-2-enyloxy)-aziridine
1-(but-2-enyloxy)-2-cyanoaziridine
1-cinnamyloxy-2-cyanoaziridine
2-cyano-1-propargyloxyaziridine
1-(but-2-ynyloxy)-2-cyanoaziridine
2-cyano-1-(1-methylprop-2-ynyloxy)-aziridine 2-cyano-1-(pent-3-ynyloxy)-aziridine
2-cyano-1-cyclopropylmethoxyaziridine
2-cyano-1-(cyclohex-3-enylmethoxy)-aziridine
2-cyano-1-cyclohexyloxyaziridine
2-cyano-1-(4-methylcyclohexyloxy)-aziridine
2-cyano-1-(4-methoxycyclohexyloxy)-aziridine
2-cyano-1-norbornyloxyaziridine
2-cyano-1-phenoxyaziridine
2-cyano-1-(3-trifluoromethylbenzyloxy)-aziridine
2-cyano-1-(3-fluorobenzyloxy)-aziridine
2-cyano-1-(4-cyanobenzyloxy)-aziridine
1-(4-tert.-butylbenzyloxy)-2-cyanoaziridine
2-cyano-1-(4-nitrobenzyloxy)-aziridine
1-(3-carbethoxybenzyloxy)-2-cyanoaziridine
1-(3-carbamoylbenzyloxy)-2-cyanoaziridine
2-cyano-1-(2-methylthiobenzyloxy)-aziridine
2-cyano-1-(2-methylsulphinylbenzyloxy)-aziridine
2-cyano-1-(2-methylsulphonylbenzyloxy)-aziridine
2-cyano-1-(4-sulphonamidobenzyloxy)-aziridine
2-cyano-1-(4-phenylbenzyloxy)-aziridine
2-cyano-1-(3,4-dichlorobenzyloxy)-aziridine
2-cyano-1-(3,4-methylenedioxybenzyloxy)-aziridine
2-cyano-1-(2-methoxy-4-nitrobenzyloxy)-aziridine
2-cyano-1-(2-hydroxy-5-nitrobenzyloxy)-aziridine
2-cyano-1-(3,4,5-trimethoxybenzyloxy)-aziridine
1-(4-acetamidobenzyloxy)-2-cyanoaziridine
1-benzhydryloxy-2-cyanoaziridine
2-cyano-1-(2-naphthyloxy)-aziridine
2-cyano-1-(2-furylmethoxy)-aziridine
2-cyano-1-(3-thenyloxy)-aziridine
2-cyano-1-(2-pyridylmethoxy)-aziridine
2-cyano-1-(2-pyrimidinylmethoxy)-aziridine
2-cyano-1-methoxy-3-methylaziridine
1-methoxy-2-cyano-3-phenylaziridine
D-(+)-2-cyano-1-[L-(−)-1-phenylethoxy]-aziridine
D-(+)-2-cyano-1-[D-(+)-1-phenylethoxy]-aziridine
L-(−)-2-cyano-1-[L-(−)-1-phenylethoxy]-aziridine
L-(−)-2-cyano-1-[D-(+)-1-phenylethoxy]-aziridine The following examples, which are given for the purpose of illustrating the present invention, describe some of the many process variants which can be used for the preparation of the compounds according to the present invention. The structures of the compounds described in the following examples were ascertained by microcombustion analyses, NMR spectra and mass spectra:

EXAMPLE 1

2-Cyano-1-ethoxyaziridine 2.98 g. Triethanolamine are added to 2.29 g. 2-bromo-3-ethoxyaminopropionitrile hydrochloride (m.p. 97°–100° C.) in 30 ml. toluene and the reaction mixture boiled under reflux for 5 hours. The toluene is then stripped off on a rotary evaporator, the residue is treated with diethyl ether, filtered and the filtrate evaporated. The residue is taken up in a little ice-cold 2N hydrochloric acid, extracted three times with diethyl ether, the ethereal phases then washed neutral with water, dried over anhydrous sodium sulphate and evaporated. The residue is then distilled. There are obtained 0.6 g. (about 53% of theory) 2-cyano-1-ethoxyaziridine; b.p. 38°–40° C. (0.1 mm.Hg.).

In an analogous manner, there are obtained from
(a) 3-benzyloxyamino-2-bromopropionitrile hydrochloride (m.p. 128°–130° C.)
  1-benzyloxy-2-cyanoaziridine (b.p. 113°–115° C./0.1 mm.Hg)
(b) 2-bromo-3-isopropoxyaminopropionitrile hydrochloride (m.p. 100°–104° C.)
  2-cyano-1-isopropoxyaziridine (b.p. 28°–29° C./0.1 mm.Hg).

EXAMPLE 2

2-Cyano-1-ethoxyaziridine

A solution of 3.3 g. triethanolamine in 10 ml. ethanol is added dropwise, with stirring, at 20° C. to 4.7 g. 2,3-dibromopropionitrile in 10 ml. ethanol. After 1 hour, a solution of 1.8 g. O-ethylhydroxylamine in 10 ml. ethanol is added dropwise and simultaneously with a solution of 3.3 g. triethanolamine in 10 ml. ethanol, whereafter the reaction mixture is boiled under reflux for 120 hours. After cooling, the reaction mixture is filtered with suction, the filtrate is evaporated and the residue is taken up in diethyl ether. The ethereal extract is shaken out twice with ice-cold 2N hydrochloric acid, washed neutral with icewater, dried over anhydrous sodium sulphate and evaporated. The residue is distilled. There is obtained 0.44 g. (about 17% of theory) 2-cyano-1-ethoxyaziridine; b.p. 38°–40° C./0.1 mm.Hg.

EXAMPLE 3

2-Cyano-1-ethoxyaziridine 1.52 g. Diazabicycloundecane is added at 0° C. to 1.93 g. 2-bromo-3-ethoxyaminopropionitrile (oily substance) in 20 ml. methylene chloride and the solution left to stand for 48 hours in a refrigerator. The reaction mixture is then evaporated and the residue is stirred with diethyl ether, filtered and the filtrate evaporated. The residue is taken up in a little ice-cold 2N hydrochloric acid, extracted three times with diethyl ether and the ethereal phases washed neutral with water, dried over anhydrous sodium sulphate and evaporated. The residue is then distilled. There is obtained 0.4 g. (about 36% of theory) 2-cyano-1-ethoxy-aziridine; b.p. 38°–40° C./0.1 mm.Hg.

EXAMPLE 4

1-(4-Chlorobenzyloxy)-2-cyanoaziridine

A solution of 3.3 g. triethanolamine in 10 ml. ethanol is added dropwise, with stirring, at 20° C. to 4.7 g. 2,3-dibromopropionitrile in 10 ml. ethanol. After 1 hour, the reaction mixture is filtered off with suction, a solution of 3.46 g. 4-chlorobenzyloxyamine in 20 ml. ethanol added to the filtrate and the reaction mixture is stirred overnight at ambient temperature. The reaction mixture is subsequently evaporated and the residue is taken up in 50 ml. methylene chloride and mixed at 0° C. with 3.34 g. diazabicycloundecene. The solution is left to stand for 48 hours in a refrigerator, then evaporated and the residue is stirred with diethyl ether, filtered with suction and the filtrate evaporated. The residue is applied to a column of silica gel (100 g.; elution agent diethyl ether/ligroin 1/1 v/v). The product thus obtained is then stirred with ligroin and filtered with suction. There is obtained 1.69 g. (about 37% of theory) 1-(4-chlorobenzyloxy)-2-cyanoaziridine; m.p. 41°–45° C.

The following compounds are obtained in an analogous manner by the reaction of 2,3-dibromopropionitrile with:
(a) phenethoxyamine
  2-cyano-1-phenethoxyaziridine (oily substance)
(b) 2-methylbenzyloxyamine 2-cyano-1-(2-methylbenzyloxy)-aziridine (m.p. 45°–49° C.)
(c) 3,4-dimethoxybenzyloxyamine
2-cyano-1-(3,4-dimethoxybenzyloxy)-aziridine (m.p. 45°–48° C.)
(d) 2-fluorobenzyloxyamine
2-cyano-1-(3-fluorobenzyloxy)-aziridine (b.p. 138°–140° C./0.1 mm.Hg)

EXAMPLE 5

Ethyl 1-ethoxyaziridine-2-carboxylate 40 g. Triethanolamine in 40 ml. ethanol are added to 69.6 g. ethyl 2,3-dibromopropionate. After 1 hour, there are simultaneously added thereto dropwise a solution of 16.3 g. O-ethylhydroxylamine in 30 ml. ethanol and 40 g. triethanolamine in 80 ml. ethanol, whereafter the reaction mixture is stirred for 12 hours at ambient temperature. The precipitate is filtered off with suction and the filtrate heated under reflux for 20 hours. The precipitate is again filtered off with suction, the filtrate is evaporated and the residue is purified over a column of silica gel (100 g. silica gel; elution agent acetone/toluene 1/1 v/v). A yellow oil is obtained which is distilled. There are obtained 25.5 g. (about 60% of theory) ethyl 1-ethoxyaziridine-2-carboxylate; b.p. 38°–40° C./0.1 mm.Hg.

The following compounds are obtained in an analogous manner by the reaction of ethyl 2,3-dibromopropionate with
(a) O-methylhydroxylamine
ethyl 1-methoxyaziridine-2-carboxylate; b.p. 42° C./0.2 mm.Hg.
(b) O-isopropylhydroxylamine
ethyl 1-isopropoxyaziridine-2-carboxylate
(c) O-n-butylhydroxylamine
ethyl 1-n-butoxyaziridine-2-carboxylate
(d) O-benzylhydroxylamine
ethyl 1-benzyloxyaziridine-2-carboxylate
(e) O-allylhydroxylamine
ethyl 1-allyloxyaziridine-2-carboxylate.

EXAMPLE 6

1-Ethoxyaziridine-2-carboxamide 22 g. Ethyl 1-ethoxyaziridine-2-carboxylate (preparation see Example 5) are dissolved in 100 ml. ethanol/100 ml. concentrated aqueous ammonia solution and left to stand for 3 days at ambient temperature. The solution is evaporated and the residue is purified over a column of silica gel (200 g. silica gel; elution agent acetone/toluene 1/1 v/v). The product obtained can be recrystallized from acetone. There are obtained 14.5 g. (about 80% of theory) 1-ethoxyaziridine-2-carboxamide; m.p. 50°–54° C.

The following compounds are obtained in an analogous manner from:
(a) ethyl 1-methoxyaziridine-2-carboxylate (see Example 5a)
1-methoxyaziridine-2-carboxamide; m.p. 83°–86° C.
(b) ethyl 1-isopropoxyaziridine-2-carboxylate (see Example 5b)
1-isopropoxyaziridine-2-carboxamide; m.p. 118°–120° C.
(c) ethyl 1-n-butoxyaziridine-2-carboxylate (see Example 5c)
1-n-butoxyaziridine-2-carboxamide; m.p. 64°–67° C.
(d) ethyl 1-benzyloxyaziridine-2-carboxylate (see Example 5d)
1-benzyloxyaziridine-2-carboxamide; m.p. 87°–90° C.
(e) ethyl 1-allyloxyaziridine-2-carboxylate (see Example 5e)
1-allyloxyaziridine-2-carboxamide; m.p. 57°–60° C.

EXAMPLE 7

1-Allyloxy-2-cyanoaziridine 25.6 g. Triphenylphosphine, 14.8 g. carbon tetrachloride and 9.8 g. triethylamine are added, while stirring at ambient temperature, to a suspension of 6.9 g. 1-allyloxyaziridine-2-carboxamide (preparation see Example 6e) in 110 ml. methylene chloride. Stirring is continued for 20 hours and then the reaction mixture is evaporated on a rotavapor. The residue is taken up in diethyl ether, filtered and the filtrate evaporated. The oily residue is applied to a column of silica gel (100 g. silica gel; elution agent acetone/toluene 1/1 v/v). There are obtained 2.6 g. of crude product which is subsequently distilled to give 1.9 g. (about 32% of theory) 1-allyloxy-2-cyanoaziridine; b.p. 58°–59° C./0.1 mm.Hg.

The following compounds are obtained in an analogous way from:
(a) 1-methoxyaziridine-2-carboxamide (see Example 6a)
2-cyano-1-methoxyaziridine (b.p. 31°–32° C./0.1 mm.Hg)
(b) 1-ethoxyaziridine-2-carboxamide (see Example 6)
2-cyano-ethoxyaziridine (b.p. 38°–40° C./0.1 mm.Hg)
(c) 1-isopropoxyaziridine-2-carboxamide (see Example 6b)
2-cyano-1-isopropoxyaziridine (b.p. 28°–29° C./0.1 mm.Hg)
(d) 1-n-butoxy-2-aziridine-2-carboxamide (see Example 6c)
1-n-butoxy-2-cyanoaziridine (b.p. 83°–84° C./0.1 mm.Hg)
(e) 1-benzyloxyaziridine-2-carboxamide (see Example 6d)
1-benzyloxy-2-cyanoaziridine (b.p. 113°–115° C./0.1 mm.Hg).

EXAMPLE 8

Sodium 1-ethoxyaziridine-2-carboxylate 1.59 g. Ethyl 1-ethoxyaziridine-2-carboxylate (preparation see Example 5) is stirred at ambient temperature for 4 hours in a mixture of 10 ml. ethanol and 20 ml. 0.5N aqueous sodium hydroxide solution. The solution is then freeze dried and the residue is taken up in water, extracted with diethyl ether and the aqueous solution again freeze dried. There is obtained 0.7 g. (46% of theory) sodium 1-ethoxyaziridine-2-carboxylate; m.p. 170° C. (decomp.).

In an analogous manner, from ethyl 1-methoxy-aziridine-2-carboxylate (preparation see Example 5a), there is obtained sodium 1-methoxyaziridine-2-carboxylate; m.p. 203° C. (decomp.).

EXAMPLE 9

In a manner analogous to that described in Example 4, the following compounds are obtained by the reaction of 2,3-dibromopropionitrile with:
(a) O-(2-bromoethyl)-hydroxylamine
1-(2-bromoethoxy)-2-cyanoaziridine (oily substance)
(b) O-(2-hydroxyethyl)-hydroxylamine
2-cyano-1-(2-hydroxyethoxy)-aziridine (oily substance)
(c) O-(2-tetrahydropyranyl)-hydroxylamine 2-cyano-1-(2-tetrahydropyranyloxy)-aziridine (oily substance)

(d) O-(2-phenoxyethyl)-hydroxylamine
2-cyano-1-(2-phenoxyethoxy)-aziridine (oily substance)

(e) 1,2-bis-(aminoxy)-ethane
1,2-bis-(2-cyano-1-aziridinyloxy)-ethane (oily substance)

(f) O-(2-methyl-2-propenyl)-hydroxylamine
2-cyano-1-(2-methyl-2-propenyloxy)-aziridine; b.p. 65°–67° C./0.1 mm.Hg (g) O-(3-propynyl)-hydroxylamine
2-cyano-1-(3-propynyloxy)-aziridine (oily substance)

(h) O-cyclohexylhydroxylamine
2-cyano-1-cyclohexyloxyaziridine (oily substance)

(i) O-(4-cyanobenzyl)-hydroxylamine
2-cyano-1-(4-cyanobenzyloxy)-aziridine; m.p. 48°–51° C. (recrystallized from ligroin)

(k) O-(2-pyridylmethyl)-hydroxylamine
2-cyano-1-(2-pyridylmethoxy)-aziridine (oily substance)

(l) O-(ethoxycarbonylmethyl)-hydroxylamine
ethyl 2-cyanoaziridin-1-yloxy acetate (oily substance)

(m) O-(4-methylbenzyl)-hydroxylamine
2-cyano-1-(4-methylbenzyloxy)-aziridine; m.p. 20° C.

(n) O-(3-α,α,α-trifluoromethylbenzyl)-hydroxylamine
2-cyano-1-(3-α,α,α-trifluoromethylbenzyloxy)-aziridine (oily substance)

(o) O-(5-chloro-2-methoxybenzyl)-hydroxylamine
1-(5-chloro-2-methoxybenzyloxy)-2-cyanoaziridine; m.p. 62°–64° C.

(p) O-(4-methoxybenzyl)-hydroxylamine
2-cyano-1-(4-methoxybenzyloxy)-aziridine; m.p. 44°–46° C.

(q) O-(2,4-dichlorobenzyl)-hydroxylamine
2-cyano-1-(2,4-dichlorobenzyloxy)-aziridine; m.p. 40°–44° C.

(r) O-(3,4-dichlorobenzyl)-hydroxylamine
2-cyano-1-(3,4-dichlorobenzyloxy)-aziridine; m.p. 48°–50° C.

(s) O-(pyrimidin-2-ylmethyl)-hydroxylamine
2-cyano-1-(pyrimidin-2-ylmethoxy)-aziridine (t) O-(pyrimidin-4-ylmethyl)-hydroxylamine
2-cyano-1-(pyrimidin-4-ylmethoxy)-aziridine

EXAMPLE 10

2-Cyano-3-methyl-1-(2-methylbenzyloxy)-aziridine 7.5 g. Triethanolamine in 50 ml. ethanol are added, with stirring, to 11.3 g. 2,3-dibromobutyronitrile in 100 ml. ethanol. After 1 hour, there are simultaneously added 7.5 g. triethanolamine in 50 ml. ethanol and 8.7 g. O-(2-methylbenzyl)-hydroxylamine hydrochloride (solid). After 24 hours, the reaction mixture is filtered with suction, the filtrate is evaporated and the residue is stirred with diethyl ether, filtered and the filtrate again evaporated. There are obtained 10 g. of an oil which is dissolved in 100 ml. anhydrous methylene chloride and mixed at 0° C. with 5.4 g. diazabicycloundecene. The reaction mixture is left to stand for 48 hours in a refrigerator, whereafter the methylene chloride is stripped off and the residue is stirred with diethyl ether, filtered and the filtrate evaporated. The oil thus obtained is separated over a column of silica gel (400 g. silica gel; elution agent diethyl ether/ligroin 1/1 v/v). There is obtained 1.06 g. (about 15% of theory) of an oil. The NMR data and the mass spectrum confirm the structure as being that of 2-cyano-3-methyl-1-(2-methylbenzyloxy)-aziridine.

EXAMPLE 11

Analogously to Example 4, by the reaction of 2,3-dibromopropionitrile with O-(3-fluorobenzyl)-hydroxylamine, there is obtained 2-cyano-1-(3-fluorobenzyloxy)-aziridine (see Example 4d). The two invertomers can be separated by column chromatographic separation on silica gel (elution agent diethyl ether/ligroin 1/1 v/v) to give:

(a) trans-2-cyano-1-(3-fluorobenzyloxy)-aziridine (oily substance) and (b) cis-2-cyano-1-(3-fluorobenzyloxy)-aziridine (oily substance).

The two invertomers are obtained in a ratio of 5:1 (trans/cis). They are clearly characterized by the NMR spectra.

EXAMPLE 12

The following examples are concerned with pharmaceutical compositions which contain compounds of general formula (I) or salts thereof:

EXAMPLE 13

Tablets.

| active material | x mg. | (x = up to 40.0 mg. |
|---|---|---|
| lactose | ad 60.0 mg. | |
| polyvinylpyrrolidone | 2.0 mg. | |
| microcrystalline cellulose | 8.0 mg. | |
| sodium carboxymethylamylopectin | 4.0 mg. | |
| highly dispersed silica acid | 0.5 mg. | |
| talc | 5.0 mg. | |
| magnesium stearate | 0.5 mg. | |
| end weight | 80.0 mg. | |

For liquid active material with dosages of up to about 40 mg.:

| active material | x mg. | (x = up to 40.0 mg.) |
|---|---|---|
| highly dispersed silicic acid | ad 100.0 mg. | |
| lactose | 135.0 mg. | |
| polyvinylpyrrolidone | 10.0 mg. | |
| microcrystalline cellulose | 25.0 mg. | |
| sodium carboxymethylamylopectin | 10.0 mg. | |
| highly dispersed silicic acid | 2.0 mg. | |
| talc | 15.0 mg | |
| magnesium stearate | 3.0 mg. | |
| end weight | 300.0 mg. | |

The active material and adjuvants are mixed, optionally granulated and pressed to give dragee cores in conventional machines. The dragee cores are then coated in the usual manner with a gastric juice-resistant, intestinal juice-soluble film (for example an anionic polymer of methacrylic acid and methyl methacrylate).

| active material | x mg. | (x = up to 40.0 mg.) |
|---|---|---|
| lactose | ad 60.0 mg. | |
| magnesium oxide | 100.0 mg. | |
| polyvinylpyrrolidone | 2.0 mg. | |
| microcrystalline cellulose | 8.0 mg. | |
| sodium carboxymethylamylopectine | 4.0 mg. | |
| highly dispersed silicic acid | 0.5 mg. | |
| talc | 5.0 mg. | |

| | |
|---|---|
| -continued | |
| magnesium stearate | 0.5 mg. |
| end weight | 180.0 mg. |

The active material and adjuvants are mixed, optionally granulated and pressed into tablets.

EXAMPLE 14

Injection solution

As compositions for injection forms which contain 2-cyano-1-methoxyaziridine, there can be mentioned aqueous solutions of polyethylene glycol 400, ethylene glycol monoethyl ether and ethanol, as well as a solution of the active material in Miglyol 812 neutral oil; the latter adjuvant is only to be used for intramuscular administration. These compositions are so formulated that the pH value, buffer capacity and titration basicity do not deviate strongly from the physiological values.

These injection solutions withstand sterilization in an autoclave for 20 minutes at 121° C. without undergoing chemical changes.

EXAMPLES

| component | amount | | | |
|---|---|---|---|---|
| 2-cyano-1-methoxyaziridine | 40 mg. | 40 mg. | 40 mg. | 40 mg. |
| polyethylene glycol 400 | 1 g. | — | — | — |
| water | 3 g. | 3 g. | 4 g. | — |
| ethylene glycol monoethyl ether | — | 2 g. | 1 g. | — |
| Miglyol 812 neutral oil | — | — | — | 3 g. |
| ethanol | 1 g. | — | — | — |

The solvents are mixed together with the active material in a kettle. The solution thus obtained is sterilized by filtration through a filter layer of Fibrafix AF. The first 15 liters are pre-runnings and are returned to the batch. The membrane filtration is carried out directly on the filling machine via a Sartorius membrane filter, pore size 0.2 μm. The solution is subsequently filled into 5 ml. ampules. The solution is sterilized in an autoclave for 20 minutes at 121° C.

EXAMPLE 15

Soft gelatine capsules

The active material is soluble in organic compounds, such as Miglyol 812 (triglyceride of saturated fatty acids with a chain length of 30 carbon atoms), mixtures of ethanol in water, polyethylene glycol 400 in water or ethylene glycol monoethyl ether in water and, in such solutions, can be worked up to give soft gelatine capsules. The active material can also be worked up in mixtures with wax, soya bean oil, lecithin and hydrogenated fats according to well-known soft gelatine capsule formulations.

| component | amount | | | | |
|---|---|---|---|---|---|
| 2-cyano-1-methoxyaziridine | 40 mg. | 40 mg. | 40 mg. | 40 mg. | 40 mg. |
| bees' wax | 20 mg. | — | — | — | — |
| hydrogenated soya bean oil | 140 mg. | — | — | — | — |
| soya lecithin | 70 mg. | — | — | — | — |
| polyethylene glycol 400 | — | 210 mg. | — | — | 180 mg. |
| Miglyol 812 | — | 100 mg. | 100 mg. | 200 mg. | 35 mg. |

| component | amount | | | | |
|---|---|---|---|---|---|
| ethylene glycol monoethyl ether | — | — | 210 mg. | 50 mg. | — |
| ethyl acetate | — | — | — | 43 mg. | 85 mg. |

The active material is mixed with the appropriate amounts of the above-mentioned adjuvants and worked up in a special machine to give soft gelatine capsules of various sizes and dosages.

EXAMPLE 16

Drops and syrups

| component | amount | | | | | |
|---|---|---|---|---|---|---|
| 2-cyano-1-methoxyaziridine | 2.5 ml. | 2.5 ml. | 2.5 ml. | 2.5 ml. | 2.5 ml. | 2.5 ml. |
| polyethylene glycol 400 | — | 9.5 ml. | 10.5 ml. | 7.5 ml. | — | 7.5 ml. |
| ethyl acetate | — | 8.0 ml. | 5.0 ml. | — | 2.5 ml. | — |
| ethylene glycol monoethyl ether | 12.0 ml. | — | — | 9.0 ml. | 3.0 ml. | 3.0 ml. |
| Miglyol 812 | 5.5 ml. | — | 2.0 ml. | 1.0 ml. | 12.0 ml. | — |
| water | — | — | — | — | — | 7.0 ml. |

| component | amount | | | |
|---|---|---|---|---|
| 2-cyano-1-methoxyaziridine | 2.5 ml. | 2.5 ml. | 2.5 ml. | 2.5 ml. |
| polyethylene glycol 400 | — | — | 12.0 ml. | — |
| ethylene glycol monoethyl ether | 2.0 ml. | — | — | 52.0 ml. |
| ethyl acetate | — | — | — | 43.0 ml. |
| Miglyol 812 | — | 154.0 ml. | — | 80.0 ml. |
| water | 134.0 ml. | — | 143.0 ml. | — |

The active material is mixed with the appropriate amount of the above-mentioned adjuvants. The mixture is sterilized by filtering through a filter layer of Fibrafix AF, as well as through membrane filters with a pore size of 0.2 μm. and the solution is filled in 20 ml. drop bottles or into 200 ml. syrup bottles.

The pharmacological properties of the new compounds were determined as follows:

Adult female Sprague-Dawley rats of Messrs. WIGA (Gassner, Sulzfeld) weighing 180–220 g were used. The animals were kept at a constant temperature ($23 \pm 1°$ C.), constant humidity of the atmosphere ($55 \pm 5\%$) and within the 12-hour day/night rhythm. The animals received rat pellets SNIFF of Messrs. Intermast, Soest, and water ad libitum. The substances to be tested (dissolved in 10 ml of 0.5% tylose solution per kg of body weight) were once orally applied to 10 rats each time, by means of a throat tube. As control, 10 rats each time were only treated with 10 ml of 0.5% tylose solution per kg of body weight. Prior to the application, the animals were kept fasting and blood was taken from the retroorbital venous plexus by means of a heparinized puncture capillary tube (B 3095/2 of Messrs. Sherwood Med. Inc., St. Louis) and the leucocytes were determined by means of a Coulter counter in known manner.

On the 4th day blood was again taken from the retroorbital venous plexus and the leucocytes were counted. The averages with standard deviations were ascertained from the individual values. The test groups were only evaluated if the control groups showed no physiological variations. Table 1 shows the value in comparison with the 1-carboxamido-2-cyanoaziridine.

The following data show that all tested substances effect a significant increase of the leucocyte number and thus are strongly immune-stimulating.

TABLE

| | Dosage of 200 mg/kg, per os | |
|---|---|---|
| | Leucocytes in Thousands | |
| Active Material of Example | 0 - Value | Maximum (after 4 days) |
| 1, 2, 3, 7b | 8.04 | 15.68 |
| 1a, 7e | 7.29 | 16.53 |
| 1b, 7c | 9.1 | 21.5 |
| 4 | 7.03 | 12.45 |
| 4a | 8.23 | 12.88 |
| 4b | 7.16 | 10.99 |
| 4d | 6.84 | 10.84 |
| 7 | 7.48 | 11.59 |
| 7a | 5.89 | 19.29 |
| 9a | 6.6 | 12.9 |
| 9e | 5.6 | 11.3 |
| 9g | 6.6 | 10.3 |
| 9i | 6.7 | 11.4 |
| 1-carboxamido-2-cyanaziridine (Comparison) | 8.9 | 9.5 |

The present invention also provides pharmaceutical compositions comprising the new compound and/or at least one solid or liquid pharmaceutical diluent or carrier.

For the preparation of pharmaceutical compositions, a N-substituted aziridine-2-carboxylic acid derivatives in accordance with the invention is mixed in known manner with an appropriate pharmaceutical carrier substance and formed, for example, into tablets or dragees or, with the addition of appropriate adjuvants, suspended or dissolved in water or an oil, for example olive oil, and placed in capsules. Since the active material is acid labile, the composition is provided with a coating which only dissolves in the alkaline medium of the intestines or an appropriate carrier material, for example a high molecular weight fatty acid or carboxymethyl-cellulose is mixed therewith. Examples of solid carrier materials include starch, lactose, mannitol, methyl cellulose, talc, highly dispersed silicic acids, high molecular weight fatty acids (for example stearic acid), gelatin, agar-agar, calcium phosphate, magnesium stearate, animal and vegetable fats and solid high molecular weight polymers (such as polyethylene glycols). Compositions suitable for oral administration can, if desired, contain flavoring and/or sweetening materials.

However, the active material is preferably injected. As injection medium, it is preferred to use water which contains the additives usual in the case of injection soultions, such as stabilizing agents, solubilizing agents and/or weakly alkaline buffers. Additives of this type include, for example, phosphate and carbonate buffers, ethanol, complex-forming agents (for example ethylenediamine-tetraacetic acid and the non-toxic salts thereof) and high molecular weight polymers (for example liquid polyethylene oxide) for viscosity regulation.

For treatment of humans the active material may be applied one or more times with each dose containing about 1 to 600 and preferably 50 to 500 mg of active material.

The synergistic effect of chloramphenicol with a selected member of the new group of compounds was determined as follows:

80 female NMRI-mice were infected with E. coli (108) diluted 1:60 by intraperitoneal application of 0,5 ml of the infecting solution each. The total number of the infected mice was split in four groups of 20 animals. Group I was used for infection control; group II was orally treated with 20 mg of chloramphenicol per kg of body weight; group III got 10 mg/kg of 2-cyano-1-methoxyaziridine (example 7a) orally and group IV was treated with both 20 mg/kg of chloramphenicol and 10 mg of 2-cyano-1-methoxyaziridine (example 7a).

The groups were observed with regard to mortality. As is shown in table 2, all animals of group I died within 4 days, whereas in group II 13 of 20 and in group IV 19 of 20 survived. 2-Cyano-1-methoxyaziridine (example 7a) alone showed a low effect (only 2 of 20 survived).

The rates of mortality did not change over a 14 days range.

TABLE 2

| | survival rate | | |
|---|---|---|---|
| | 1st day | 4th day | 14th day |
| chloramphenicol 20 mg/kg | 13/20 | 13/20 | 13/20 |
| 2-cyano-1-methoxy-aziridine 10 mg/kg | 2/20 | 2/20 | 2/20 |
| chloramphenicol 20 mg/kg + 2-cyano-1-methoxy-aziridine 20 mg/kg | 20/20 | 19/20 | 19/20 |
| control | 1/20 | 0/20 | 0/20 |

It will be appreciated that the instant specification and examples are set forth by way of illustration and not limitation, and that various modifications and changes may be made without departing from the spirit and scope of the present invention.

We claim:

1. A compound having the formula

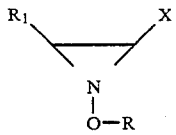

wherein X is a carboxyl, a cyano, an alkoxycarbonyl or a carbamoyl radical optionally substituted by lower alkyl, cycloalkyl, aryl and/or acyl, R is a hydrogen atom, an aliphatic hydrocarbon radical of up to 8 carbon atoms which is substituted up to three times by halogen, alkoxy, hydroxyl, dialkylamino, dialkylaminoxy, cycloalkylamino, acylamino, acyl, nitro, alkylthio, alkylsulphinyl, alkylsulphonyl, cyano, carboxyl, alkoxycarbonyl and carbamoyl or by cycloalkyl or cycloalkenyl radicals optionally carrying up to three alkyl, alkoxy and alkoxycarbonyl radicals, or by norbornyl, adamantyl, tetrahydrofuryl, tetrahydropyranyl or thienyl, or by an aryl, hetaryl, aryloxy, arylthio, acyloxy, alkoxycarbonylamino and isothio-ureido radical, or R is a cycloalkyl or cycloalkenyl radical optionally substituted by up to three alkyl, alkoxy and oxo groups, or is norbornyl, adamantyl, tetrahydrofuryl, tetrahydropyranyl or thienyl, or is a hetaryl radical which can be substituted up to three times by halogen, alkoxy, alkyl, hydroxyl, alkoxycarbonyl, carbamoyl, dialkylamino, cycloalkylamino, acylamino, nitro, cyano, acyl, alkylthio, alkylsulphinyl, alkylsulphonyl, sulphamoyl, phenyl, trifluoromethyl, aryloxy, acyloxy or methylenedioxy radicals, and $R_1$ is a hydrogen atom or an alkyl or phenyl radical, with the proviso that when X is carbamoyl or an alkoxycarbonyl radical and $R_1$ is a hydrogen atom, R is not a benzyl radical, acyl as employed hereinabove being selected from the group consisting of formyl, acetyl, benzoyl, furoyl, tosyl, and methylsulphonyl, hetaryl as employed hereinabove being pyridyl, quinolyl, furyl, thienyl, benzofuryl, imidazolyl, pyrazolyl, thiazolyl, pyrimidinyl, pyridazinyl, s-triazolyl, 3-triazinyl or purinyl, alkyl as employed hereinabove unless otherwise specified containing up to 8 carbon atoms, cycloalkyl and cycloalkenyl as employed hereinabove containing 3 to 10 carbon atoms, and aryl being selected from the group consisting of phenyl, napthyl, anthracenyl, phenanthrenyl and fluorenyl; or a pharmacologically acceptable salt thereof.

2. A compound or salt according to claim 1, in which X is a carboxyl, a nitrile or a substituted carbamoyl radical.

3. A compound or salt according to claim 1, in which $R_1$ is a $C_{1-6}$-alkyl or phenyl radical.

4. A compound or salt according to claim 1, in which said compound is 1-(4-chlorobenzyloxy)-2-cyanoaziridine of the formula

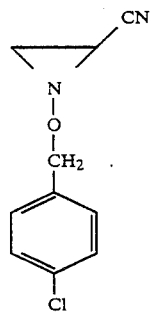

5. A compound or salt according to claim 1, in which said compound is 2-cyano-1-(2-methylbenzyloxy)-aziridine of the formula

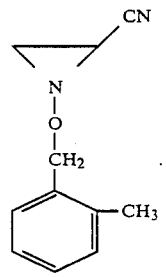

6. A compound or salt according to claim 1, in which said compound is 2-cyano-1-(3.4-dichlorobenzyloxy)-aziridine of the formula

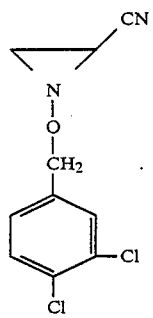

7. A compound or salt according to claim 1, in which said compound is 1-(2-bromoethoxy)-2-cyanoaziridine of the formula

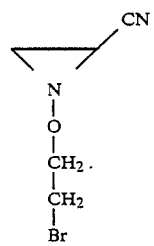

8. A compound or salt according to claim 1, in which said compound is 2-cyano-1-(4-cyanobenzyloxy)-aziridine of the formula

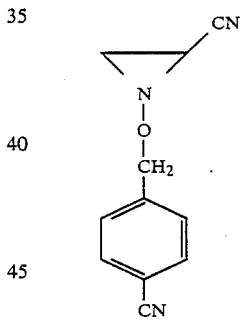

9. An immunostimulating composition of matter consisting essentially of an immunostimulating effective amount of a compound or salt according to claim 1 in admixture with a pharmaceutically acceptable diluent.

10. A method of stimulating the immunoresponsive system of a patient which comprises administering to said patient an immunostimulating effective amount of a composition according to claim 9.

11. The method according to claim 10, in which the active compound is
1-(4-chlorobenzyloxy)-2-cyanoaziridine,
2-cyano-1-(2-methylbenzyloxy)-aziridine,
2-cyano-1-methoxyaziridine,
1-(2-bromoethoxy)-2-cyanoaziridine,
2-cyano-1-(4-cyanobenzyloxy)-aziridine,
1-(5-chloro-2-methoxybenzyloxy)-2-cyanoaziridine,
2-cyano-1-(2,4-dichlorobenzyloxy)-aziridine, or
2-cyano-1-(3,4-dichlorobenzyloxy)-aziridine
or a pharmacologically acceptable salt thereof.

12. A compound or salt according to claim 1, in which said compound is 1-(5-chloro-2-methoxybenzyloxy)-2-cyanoaziridine of the formula
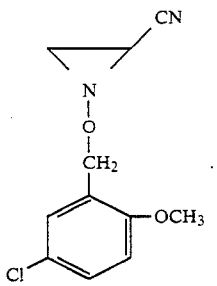
13. A compound or salt according to claim 1, in which said compound is 2-cyano-1-(2,4-dichlorobenzyloxy)-aziridine of the formula
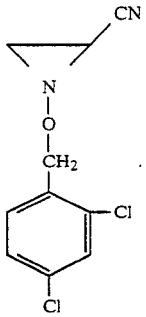
* * * * *